US012606518B2

(12) United States Patent
Ryu et al.

(10) Patent No.: US 12,606,518 B2
(45) Date of Patent: Apr. 21, 2026

(54) CRYSTALLINE FORM OF L-SERINE AND PROCESS OF PREPARING SAME

(71) Applicant: ASTROGEN, INC., Daegu (KR)

(72) Inventors: Hyung Chul Ryu, Daegu (KR); Su-Kyeong Hwang, Daegu (KR)

(73) Assignee: ASTROGEN, INC., Daegu (KR)

(*) Notice: Subject to any disclaimer, the term of this patent is extended or adjusted under 35 U.S.C. 154(b) by 0 days.

(21) Appl. No.: 18/947,046

(22) Filed: Nov. 14, 2024

(65) Prior Publication Data

US 2026/0015312 A1 Jan. 15, 2026

(30) Foreign Application Priority Data

Jul. 10, 2024 (KR) ........................ 10-2024-0091387

(51) Int. Cl.

*C07C 229/22* (2006.01)
*C07C 227/42* (2006.01)

(52) U.S. Cl.

CPC .......... *C07C 229/22* (2013.01); *C07C 227/42* (2013.01)

(58) Field of Classification Search

None

See application file for complete search history.

(56) References Cited

U.S. PATENT DOCUMENTS 5,382,517 A 1/1995 Ura et al.
2024/0173253 A1 5/2024 Nam et al.

FOREIGN PATENT DOCUMENTS

CN 108558690 B 4/2021
CN 116715598 A * 9/2023 .......... C07C 227/40
KR 10-1948066 B1 2/2019
KR 10-2022-0131186 A 9/2022

OTHER PUBLICATIONS

Aswathappa ("Acoustic shock wave-induced dynamic recrystallization of amino acids: a case study on L-serine" CrystEngComm, published May 19, 2024, p. 3331) (Year: 2024).*

Luk ("Solubilities of and Transformations between the Anhydrous and Hydrated Forms of L-Serine in Water-Methanol Solutions", Crystal Growth and Design, 2006, p. 1808) (Year: 2006).*

Alabanza (Crystallization of Amino Acids on a 21-well Circular PMMA Platform Using Metal-Assisted and Microwave-Accelerated Evaporative Crystallization, Nano Biomed. Eng. 2013, p. 147-154, including Supporting Information (SI) p. S1-S7) (Year: 2013).*

Machine generated English language translation of CN 1167115598A (Year: 2025).*

Luo, et al., "Hygroscopicity of amino acids and their effect on the water uptake of ammonium sulfate in the mixed aerosol particles", Science of Total Environment, 2020, vol. 734, pp. 1-10 (10 pages).

Nageshwari, et al., "Growth and characterization of L-Serine: A promising acentric organic crystal", Physica B: Physics of Condensed Matter, 2018, pp. 1-42 (43 pages).

(Continued)

*Primary Examiner* — Amy C Bonaparte
(74) *Attorney, Agent, or Firm* — Sughrue Mion, PLLC

(57) ABSTRACT

A novel crystalline form of L-serine and a method for preparing the same are disclosed. The novel crystalline form of L-serine has improved hygroscopicity and can be usefully used in the preparation of pharmaceutical agents.

12 Claims, 15 Drawing Sheets

(56) References Cited

OTHER PUBLICATIONS

Ikeda, et al., "Amino Acid Production Processes", Advances in Biochemical Engineering/Biotechnology, 2003, vol. 79, pp. 1-35 (35 pages).
Carter, et al., "Working with Hazardous Chemicals", Organic Syntheses Inc., vol. 20, 1940, (6 pages).
Bazeera et al., "Structural, Linear and Nonlinear Optical Properties of L-Serine Single Crystal", National Conference on Recent Developments in Effective Materials (REDEEMS-18) organized by Department of Physics, Sarah Tucker College (Autonomous), Tirunelveli, TamilNadu, Feb. 19, 2018, Special Issue Published in International Journal of Trend in Research and Development (IJTRD), ISSN: 2394-9333.
Boldyreva et al., "Pressure-induced phase transitions in crystalline L-serine studied by single-crystal and high-resolution powder X-ray diffraction", Chemical Physics Letters 429, 2006, 474-478.
Moggach et al., "Effect of pressure on the crystal structure of L-serine-I and the crystal structure of L-serine-II at 5.4 GPa", Acta Cryst., 2005, B61, 58±68.
Sander et al., "Sonocrystallization and sonofragmentation", Ultrasonics Sonochemistry 21, 2014, 1908-1915.
Chakraborty et al., "Drying induced polymorphic transformation of pharmaceutical ingredients: a critical review of recent progresses and challenges", Drying Technology, 2021, https://doi.org/10.1080/07373937.2021.1983823.
Airaksinen et al., "Comparison of the effects of two drying methods on polymorphism of theophylline", International Journal of Pharmaceutics 276, 2004, 129-141.
Wang et al., "Highly Crystalline Forms of Valsartan with Superior Physicochemical Stability", dx.doi.org/10.1021/cg400762w, Cryst. Growth Des., 2013.

* cited by examiner

[Fig. 1]
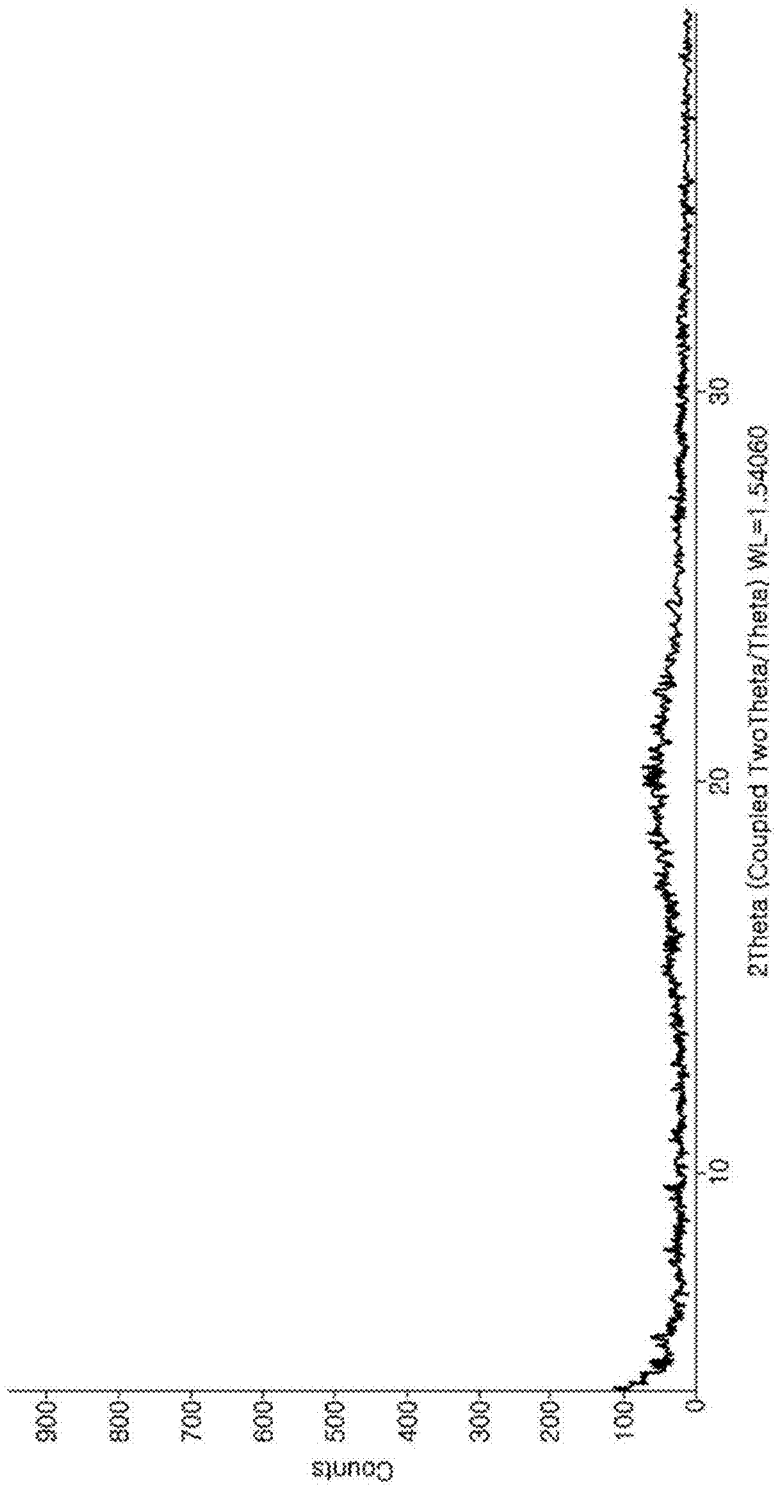

[Fig. 2]
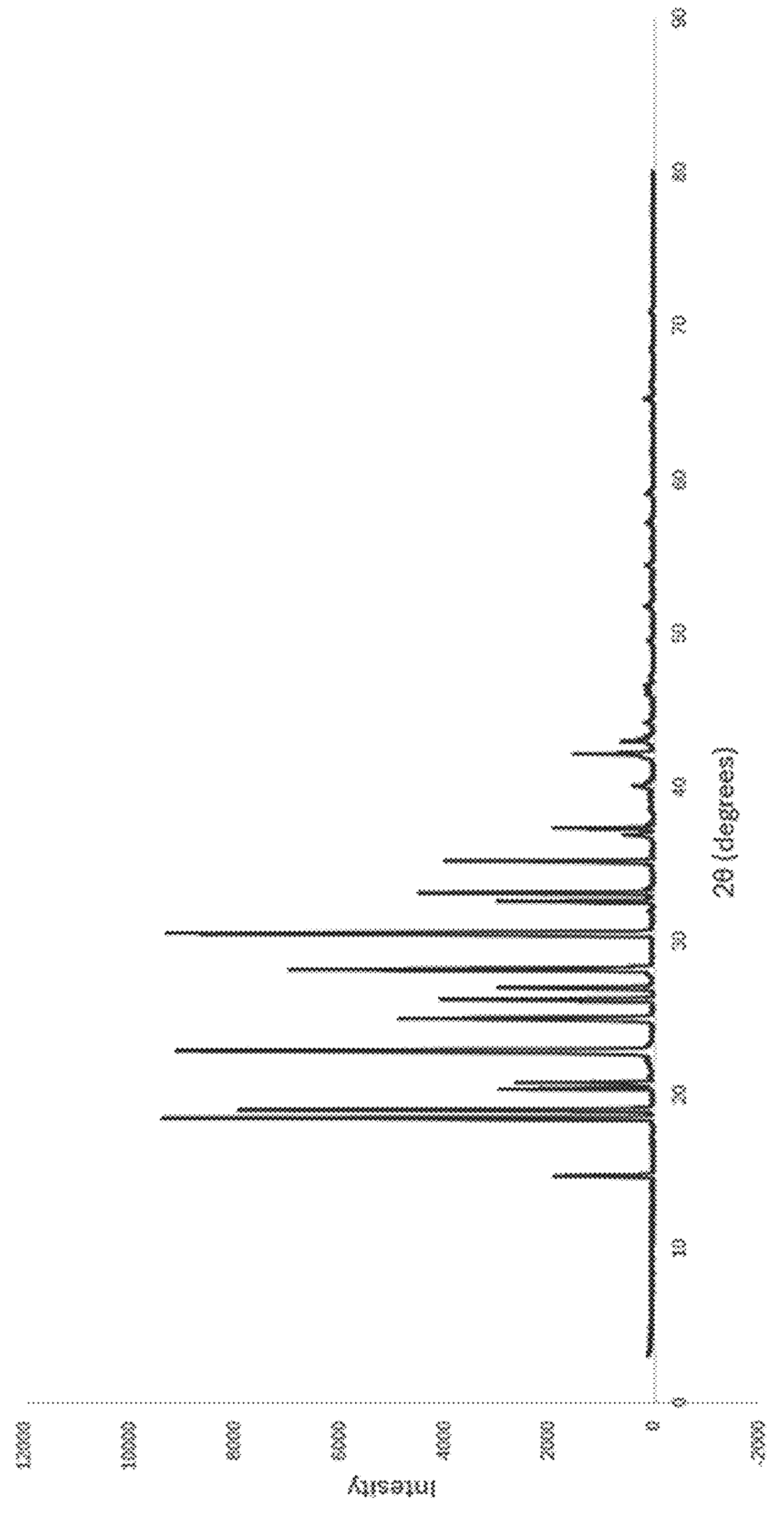

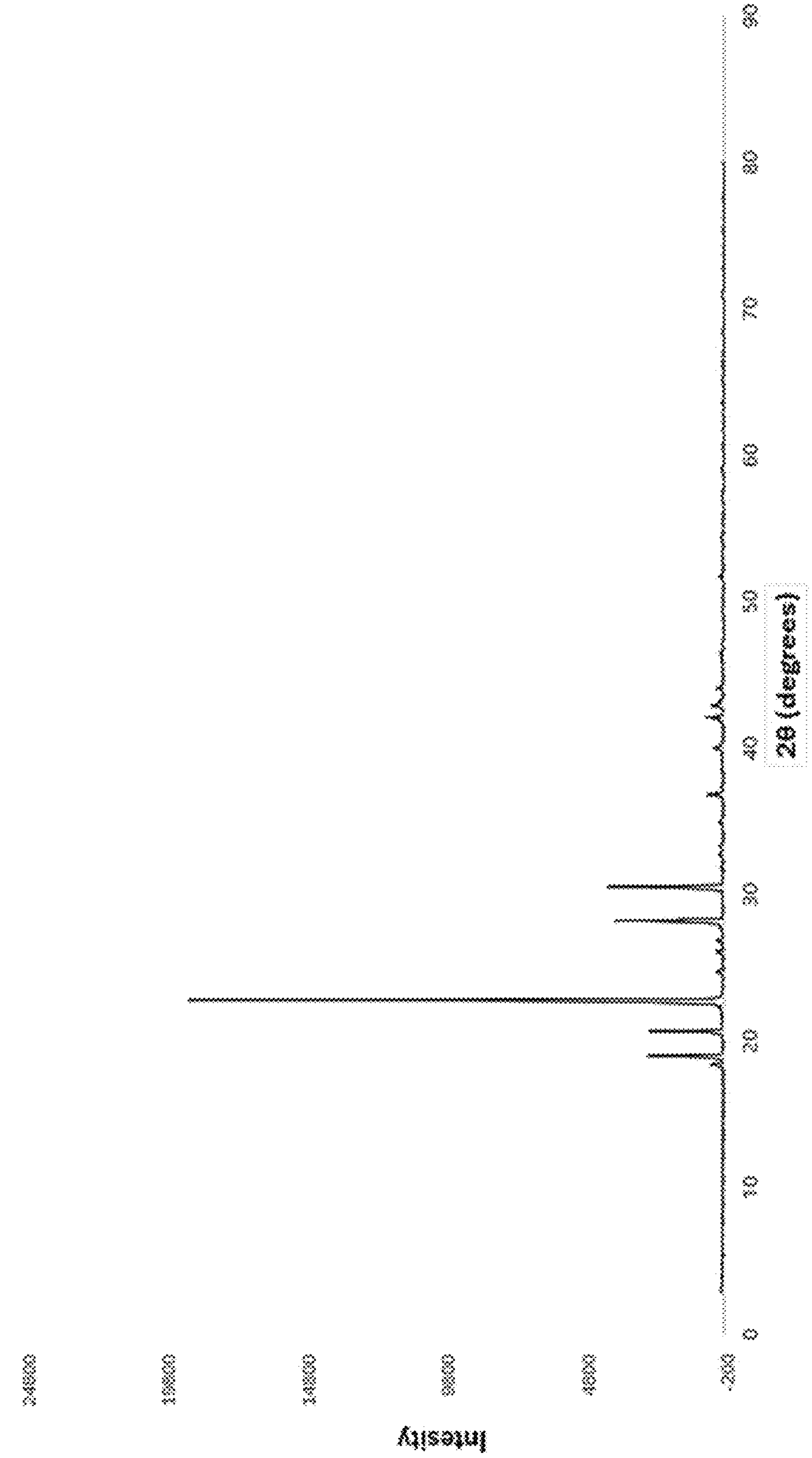
[Fig. 3]

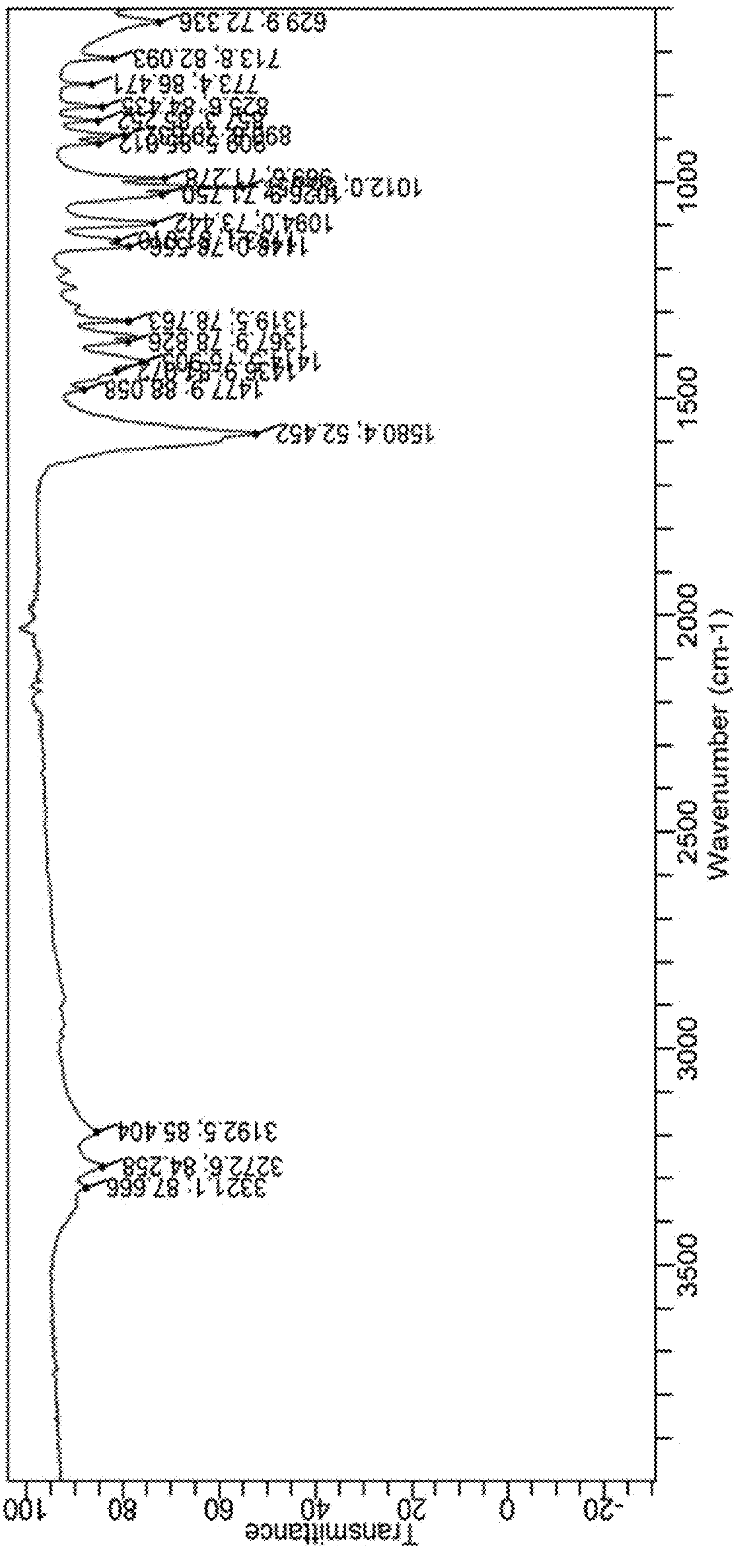
[Fig. 4]

[Fig. 5]
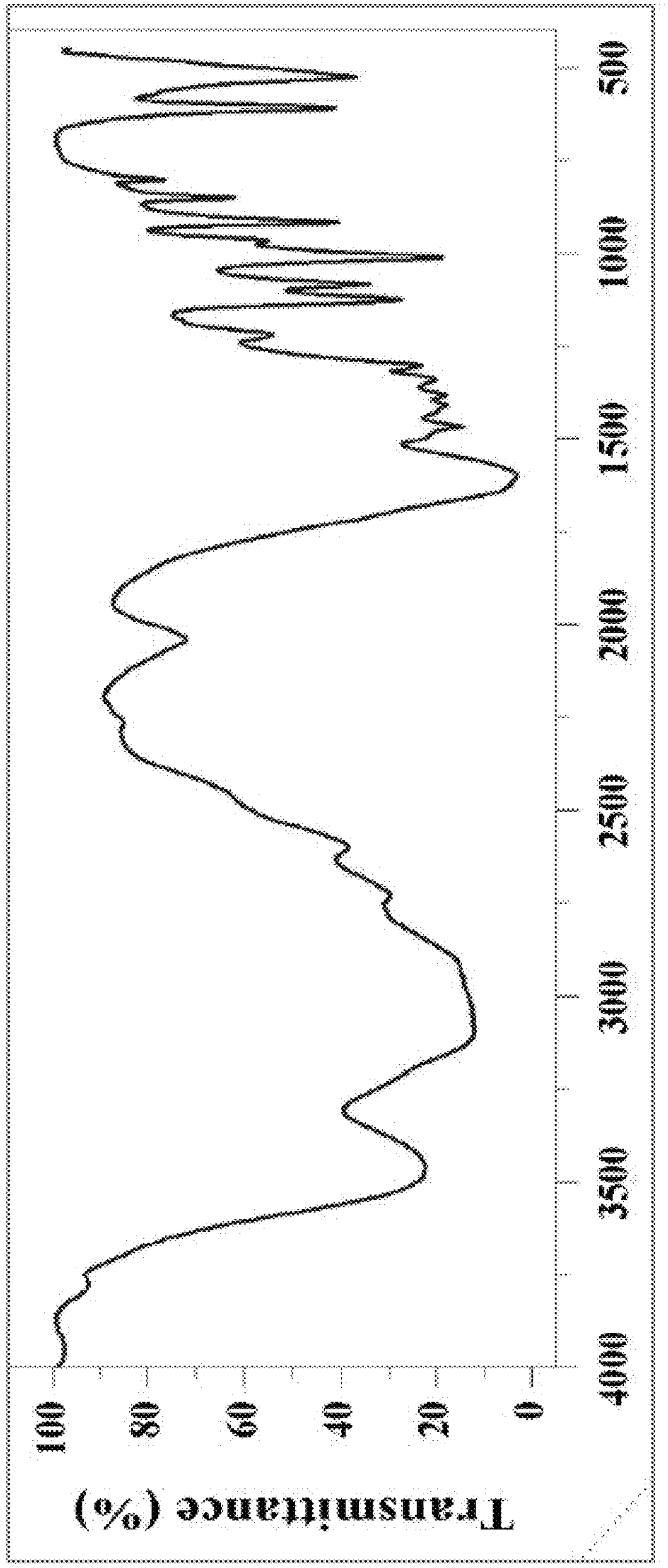

[Fig. 6]
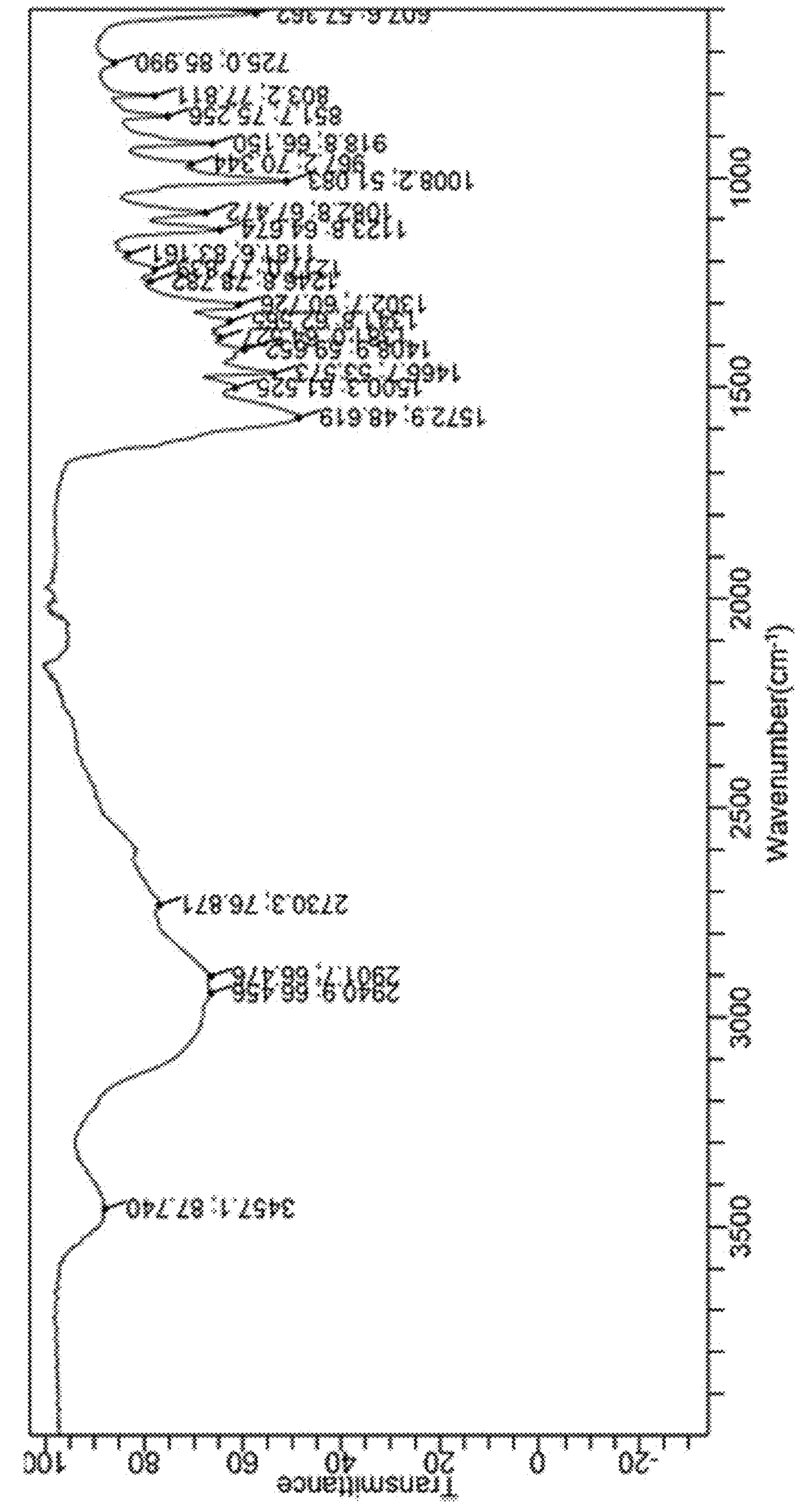

[Fig. 7]
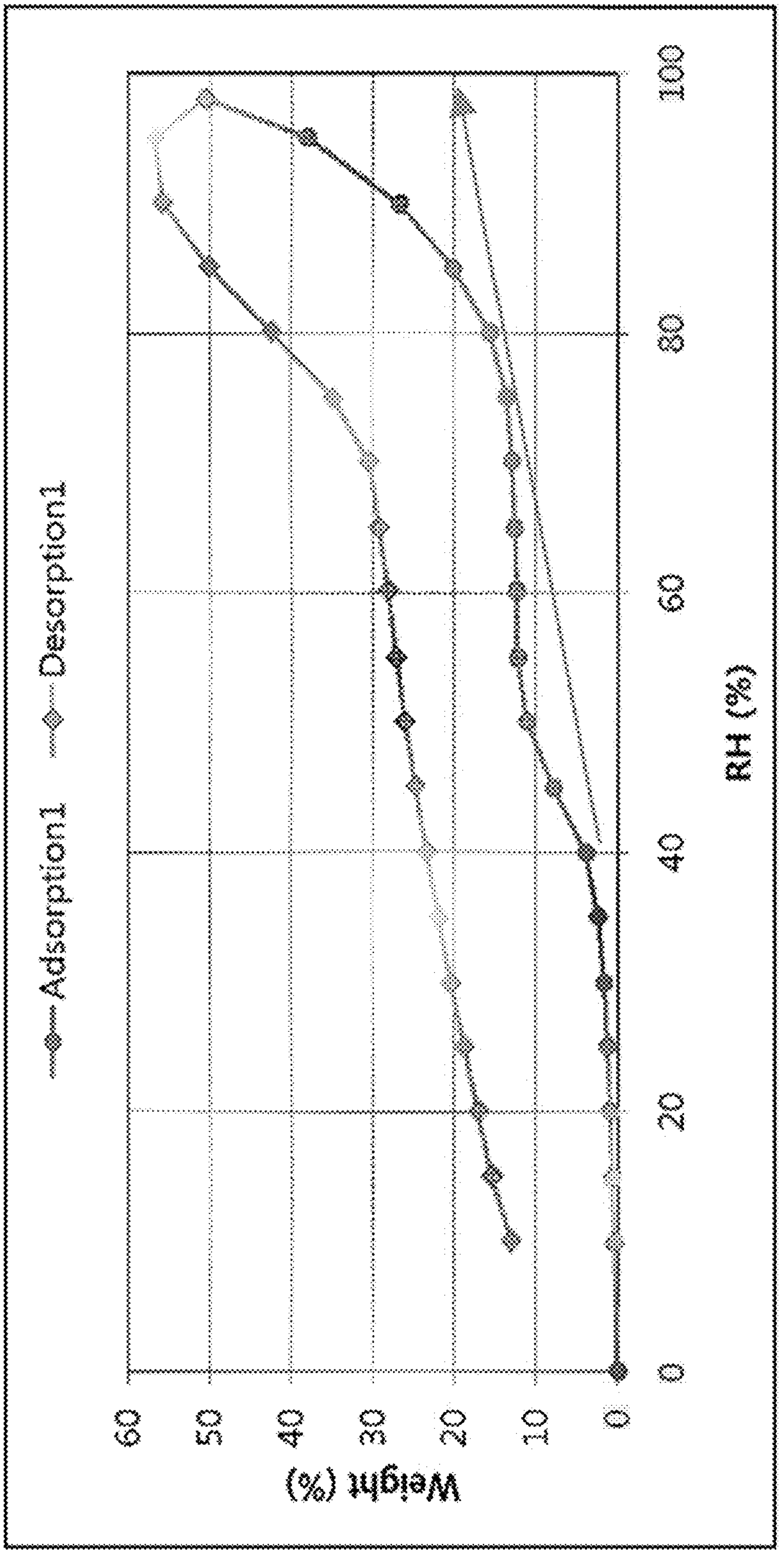

[Fig. 8]
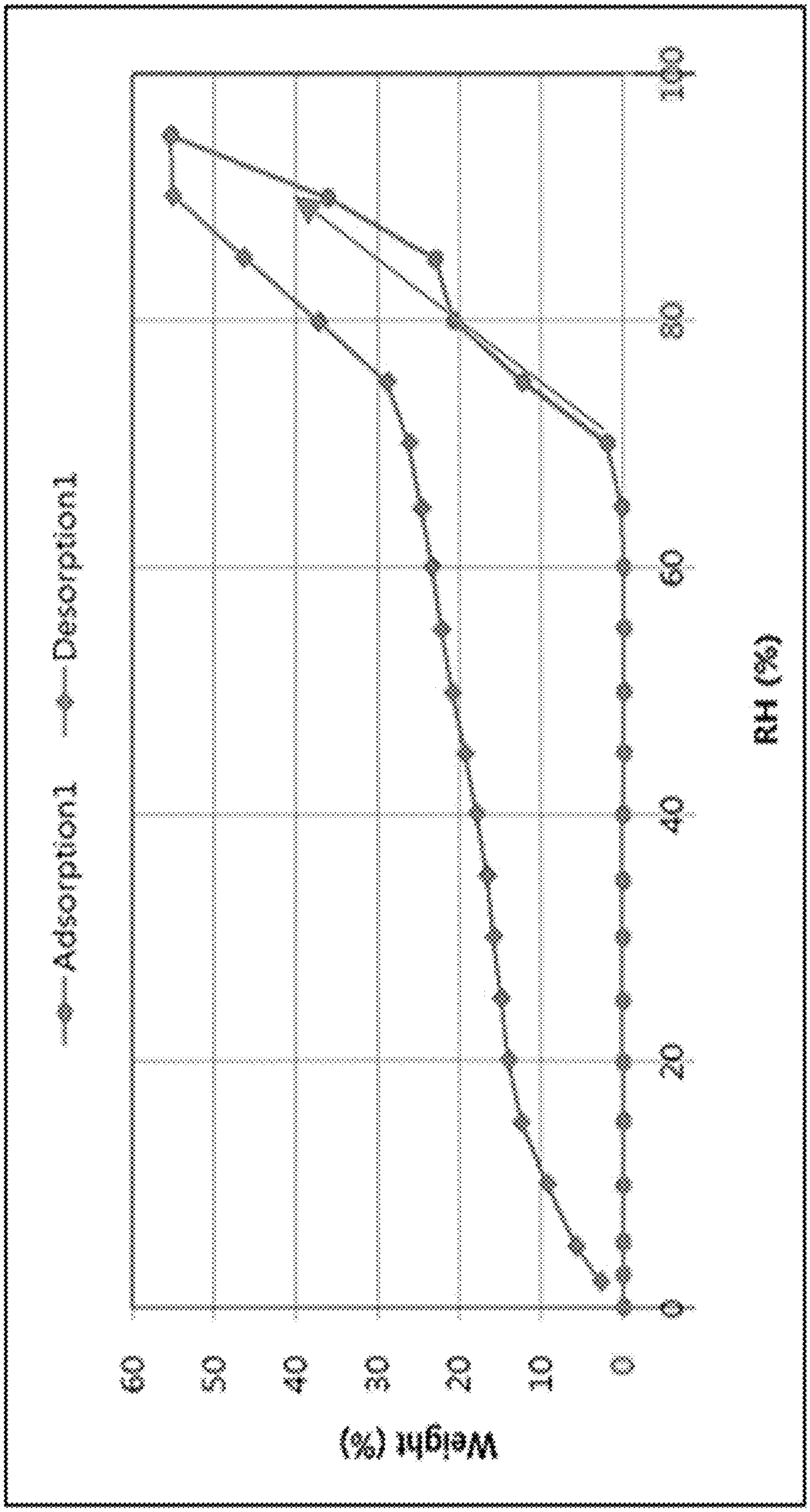

[Fig. 9]
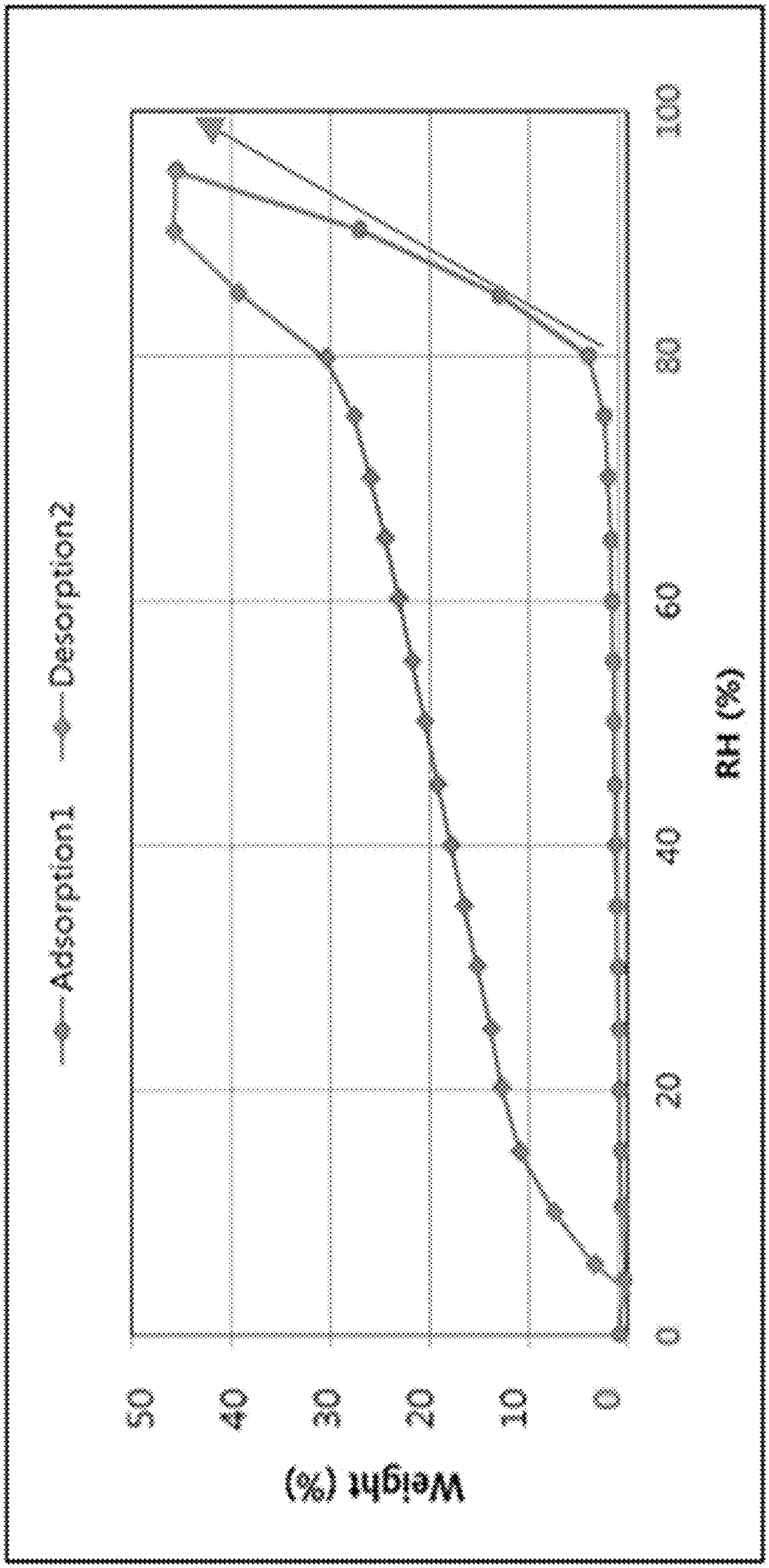

[Fig. 10]
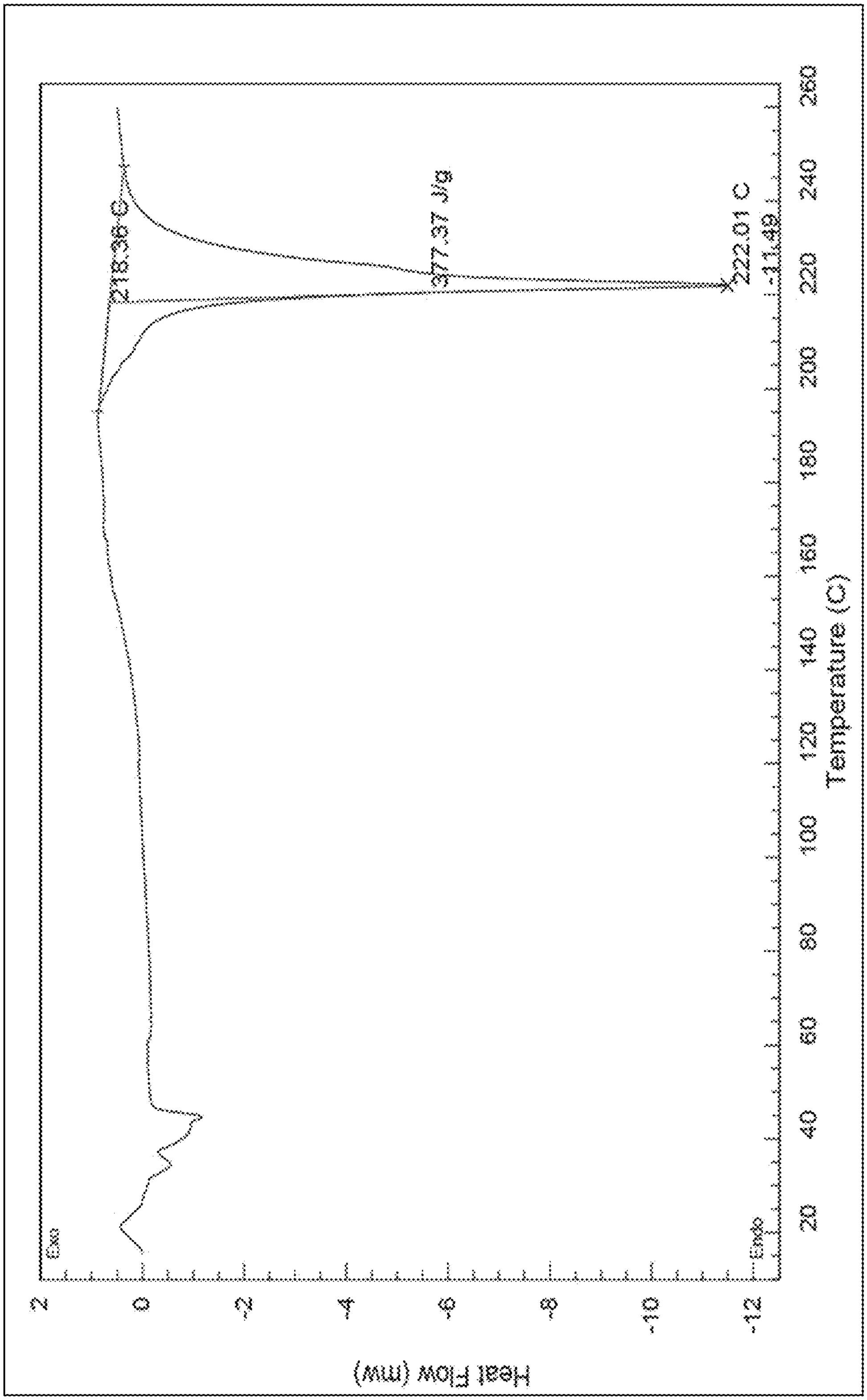

[Fig. 11]
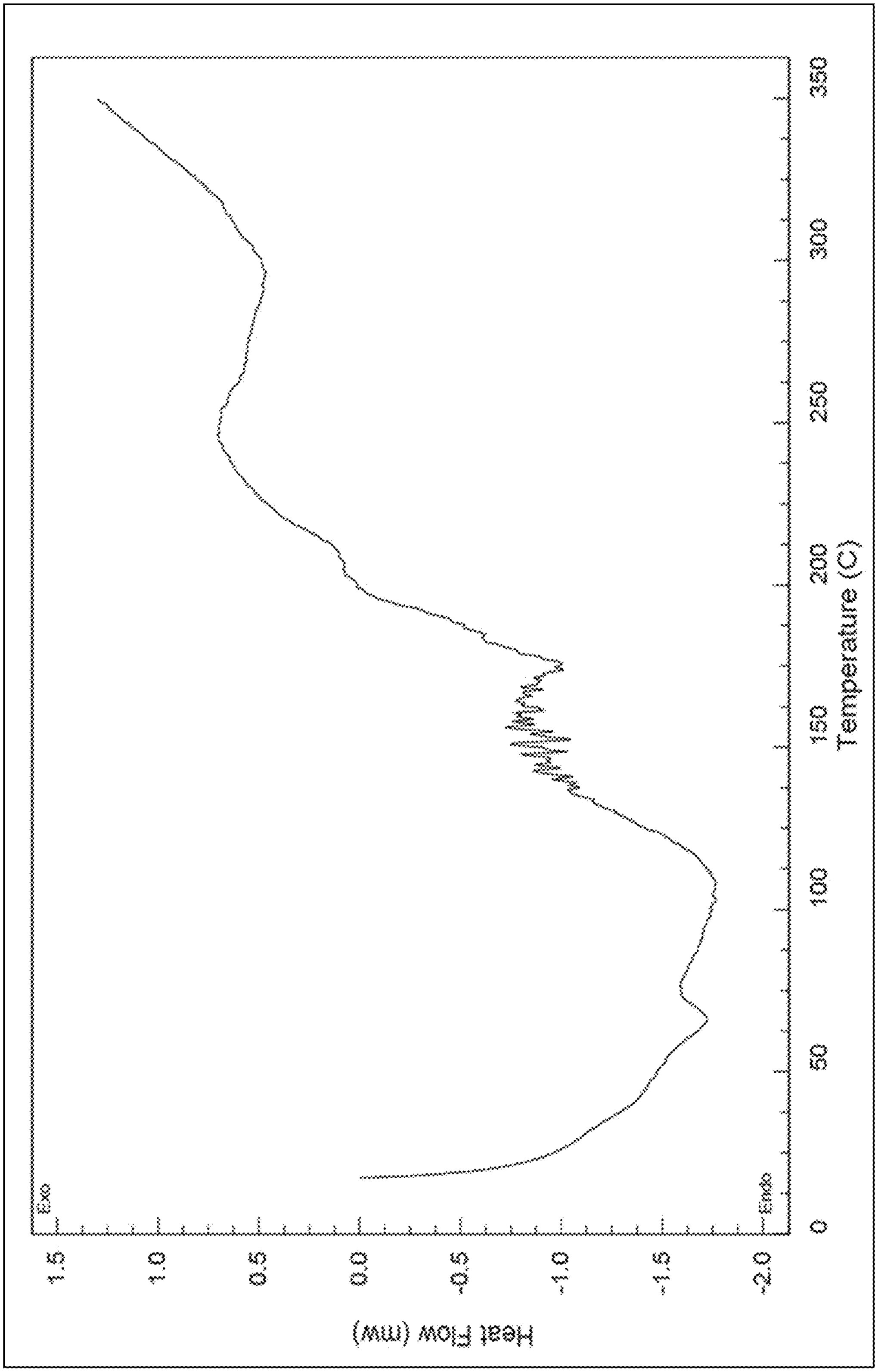

[Fig. 12]
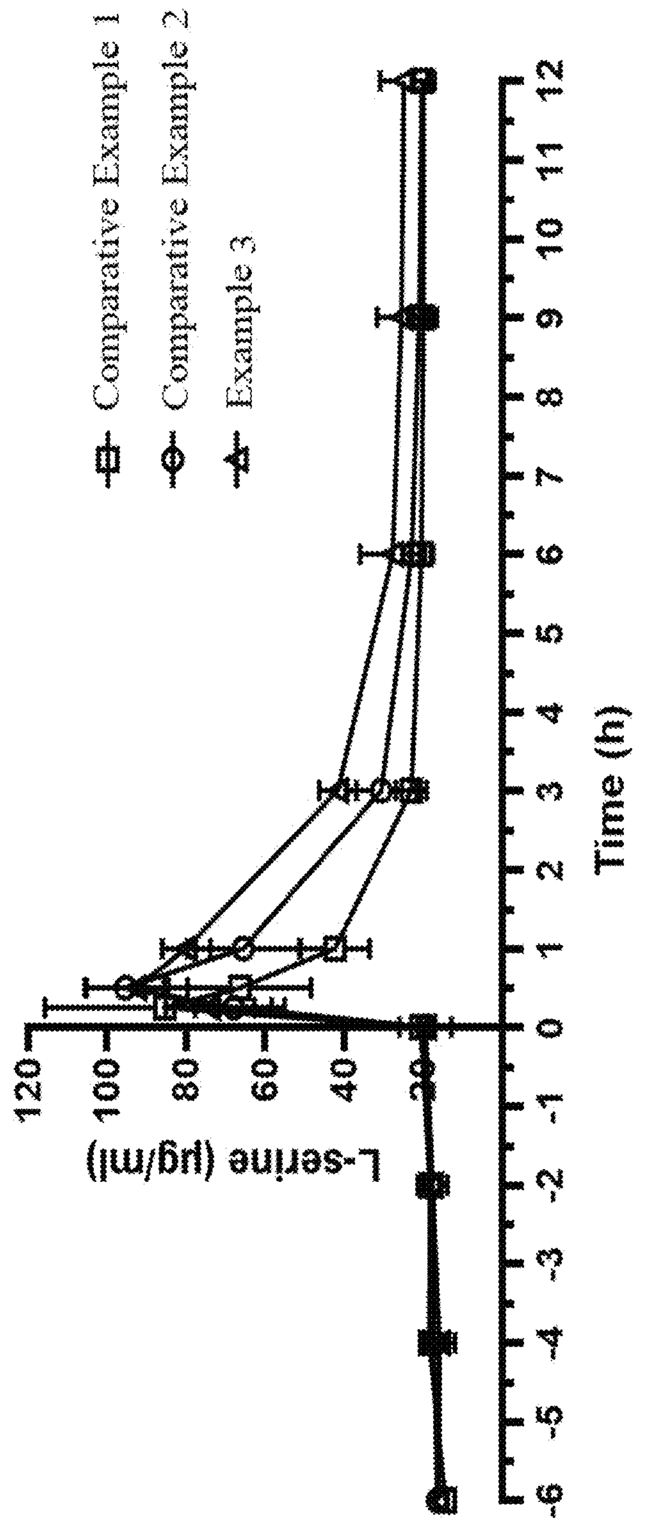

[Fig. 13]
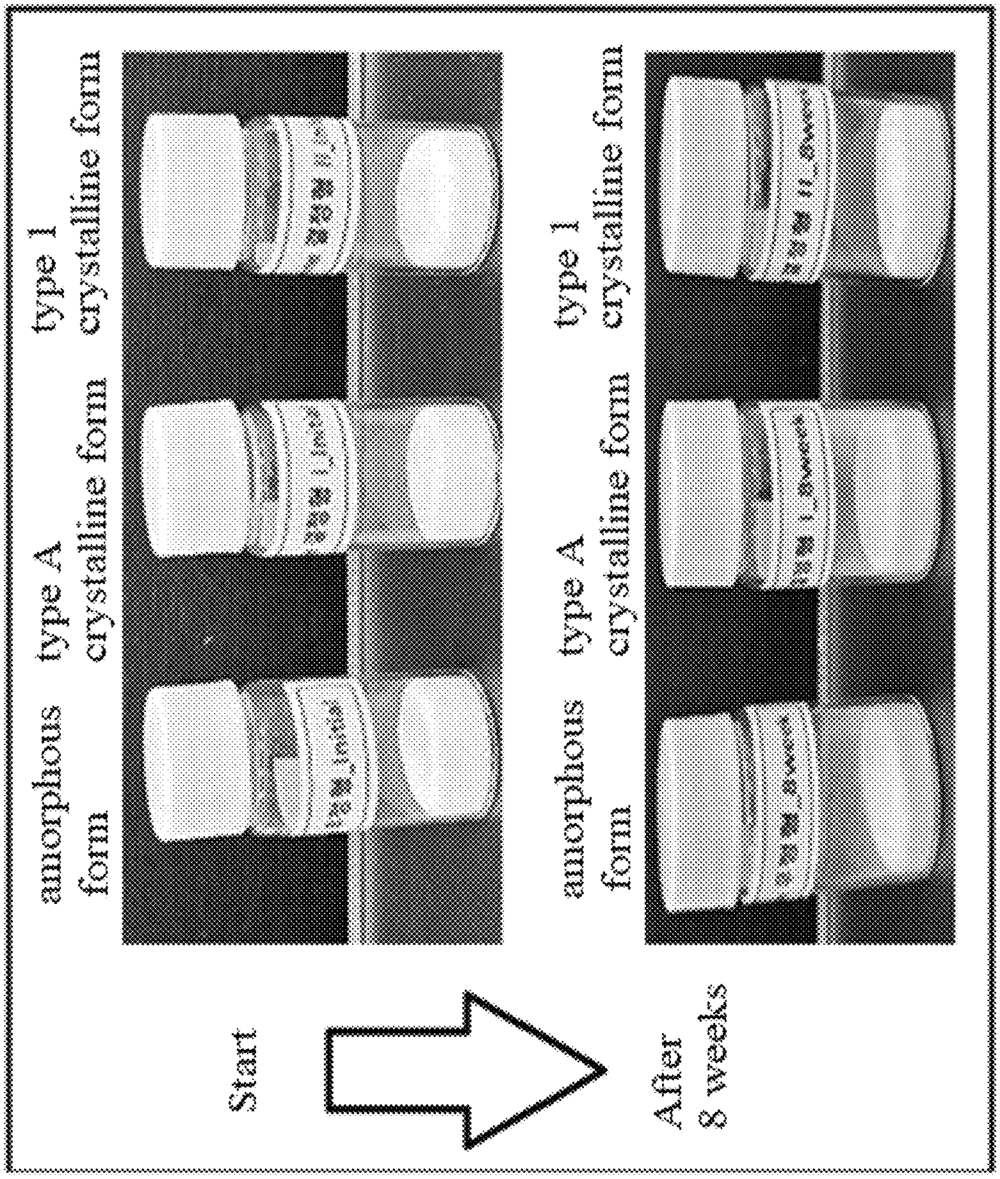

[Fig. 14]
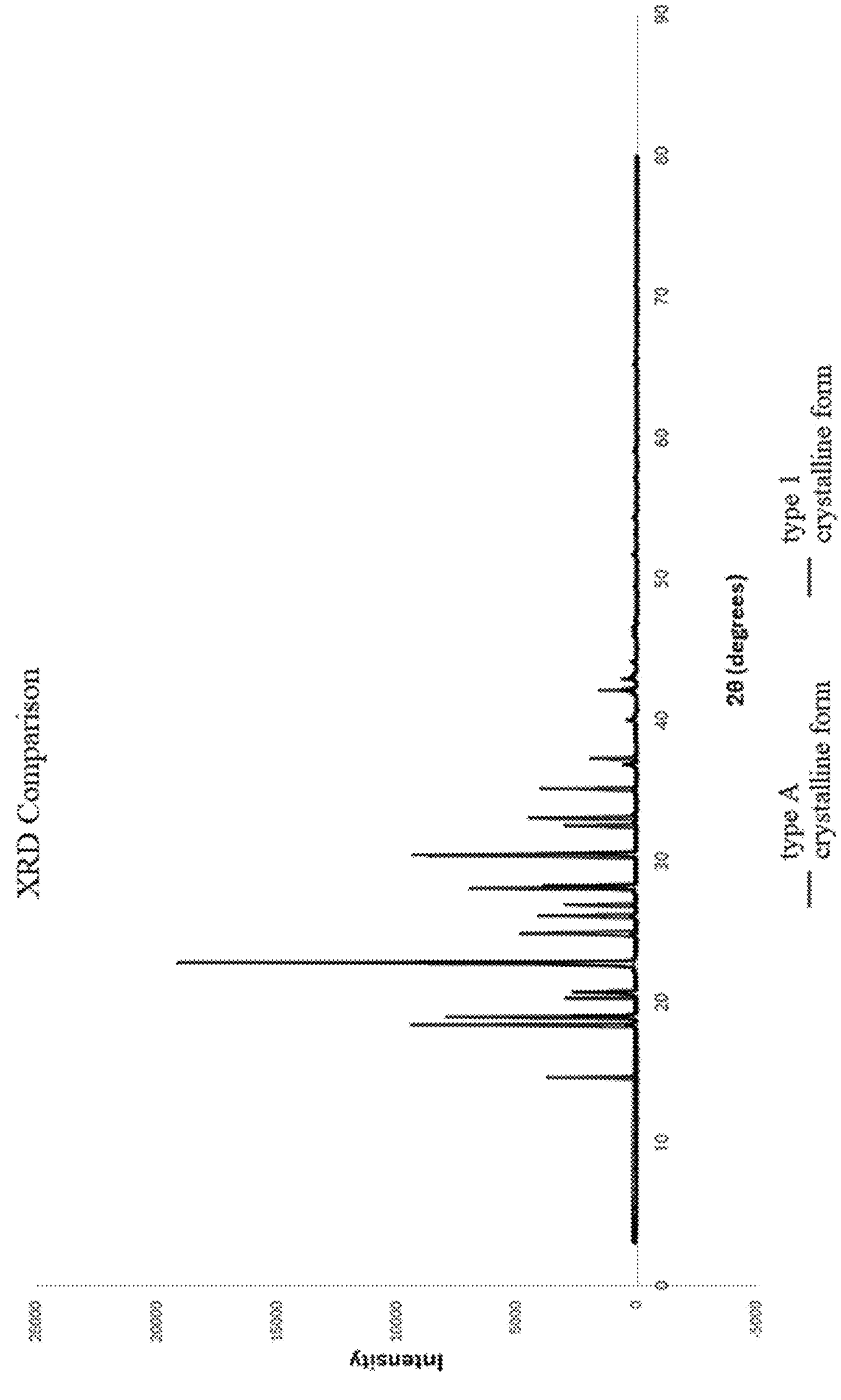

[Fig. 15]
PRIOR ART
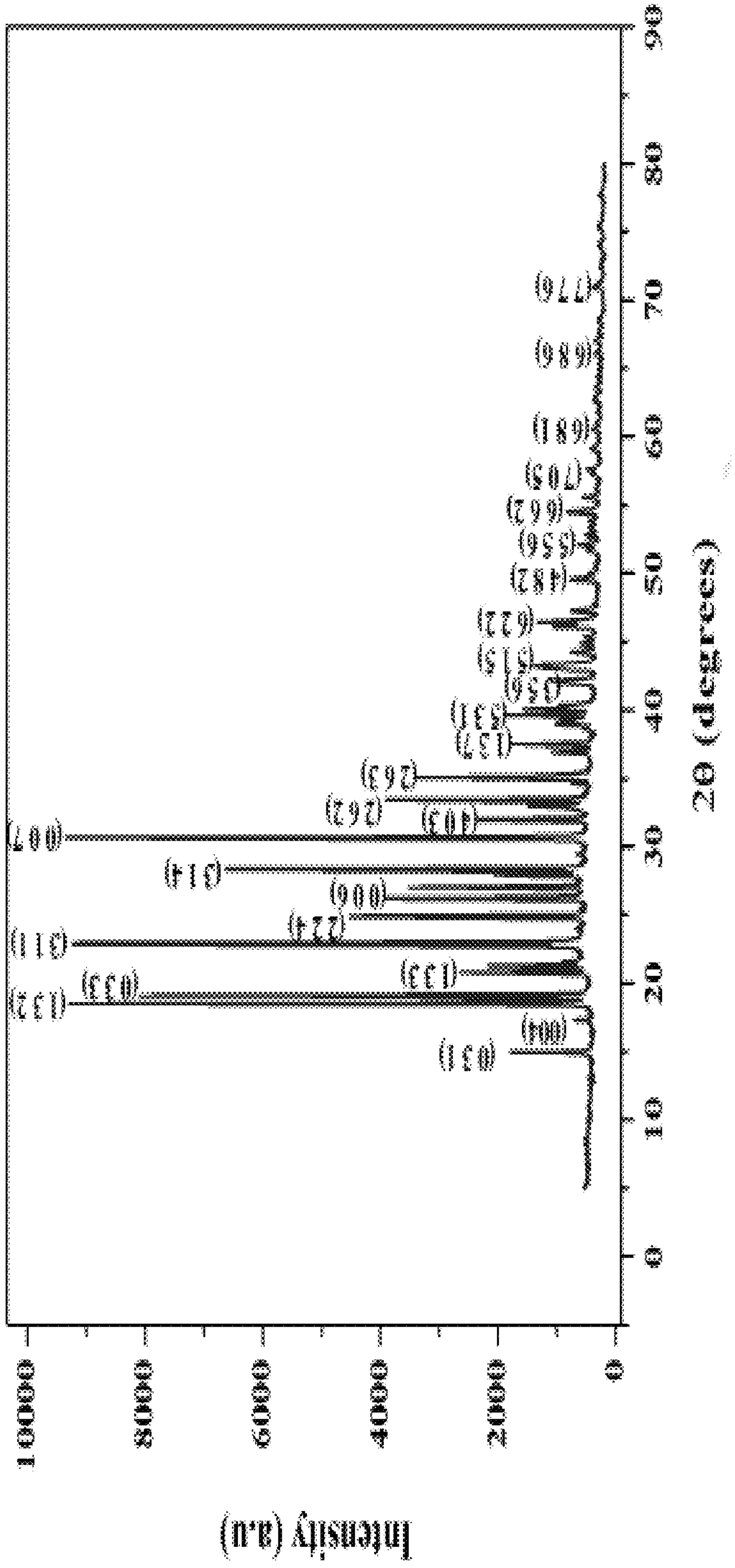

CRYSTALLINE FORM OF L-SERINE AND PROCESS OF PREPARING SAME

CROSS REFERENCE TO RELATED APPLICATIONS

This application claims priority to and benefits of Korean Patent Application No. 10-2024-0091387 filed Jul. 10, 2024, of which the entire content is incorporated herein by reference.

TECHNICAL FIELD

The present invention relates to a novel crystalline form of L-serine and a method of preparing the same. More specifically, the present invention relates to a novel crystalline form of L-serine with improved stability through improved hygroscopicity, thereby having improved properties of storage and handling, and improved dissolution rate, solubility, and pharmacokinetic characteristics, and a method of preparing the same.

BACKGROUND ART

L-Serine, represented by Formula 1 below, is a non-essential amino acid that is involved in many metabolic systems and plays an important role in the normal growth and development of nerve cells, and it plays an essential role in cell proliferation by synthesizing bases that become the ingredients of DNA, and also plays an important role in antioxidation by acting as a precursor for glutathione synthesis.

In the Korean Patent No. KR101948066B1, the contents regarding a composition for preventing, improving, or treating neurodevelopmental disorders containing L-serine as an active ingredient are disclosed, in which the administration of L-serine required for effective treatment is 200 mg/kg to 400 mg/kg twice a day. Meanwhile, Korean Patent Publication No. 10-2022-0131186 discloses a syrup agent form, which is an optimal drug formulation that can be consumed by children with autism spectrum disorder.

L-serine is known to be a white solid that is highly soluble in water and decomposes at a melting point of 246° C.

[Formula 1]

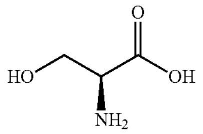

For the formulation of medicines and health functional foods containing active ingredients, it is important to deliver an effective amount of active ingredients at an appropriate time and maintain the concentration in the body so that the effect can be achieved, regardless of the route of administration of medicine or health functional food.

Most of the active ingredients of new therapeutic substances exist in solid form, and they may be amorphous or crystalline. The solid particles of each drug have different hardness, shape, size, and density, and thus their activity and stability are also various.

The physical form of the active ingredient not only affects the difficulty in formulation, but also affects stability before and after formulation and biological activity in the human body after the administration of the drug. Therefore, regardless of the structure and mechanism of action (MOA) of the drug, the optimal form of the active ingredient should be selected to ensure that the structure and composition of the drug are maintained when formulating a new drug.

In particular, as revealed through the inventors' earlier invention, in the case of L-serine, which is an active ingredient in solid form, the dose required to show its efficacy is as large as 200-400 mg/kg; therefore, it is essential to develop a crystalline form with optimized solid stability and biochemical activity. Additionally, the present inventors have identified the effect of L-serine for treating developmental disorders through Korean Patent No. KR101948066B1. In developing L-serine as a pharmaceutical preparation for its easy administration to pediatric patients, a variety of dosage forms capable of providing ease of administration are essential for patients with developmental disorders in children who have many eating disorders; therefore, the dissolution rate, solubility, and pharmacokinetics of solids are more important factors.

In general, the amorphous form has high solubility, which helps increase drug efficacy and quick efficacy, but it is unstable, thus shortening the shelf life, and also making it difficult to release the drug and control blood concentration. Meanwhile, the crystalline form has low solubility and thus low bioavailability per unit weight, but has advantages in that it can ensure stability thus being capable of preparing a sustained controlled-release formulation.

According to a Non-Patent Document 1 (*Science of The Total Environment*, vol 11, 2020, 139318), it can be seen that the hygroscopicity of amino acids is closely associated with water solubility. In the case of L-serine, it has a relatively high water solubility of 50 g/kg; therefore, the increase in hygroscopicity is relatively higher than that of aspartic acid or glutamine, which are the amino acids in the comparison group, depending on the relative humidity.

Non-Patent Document 2 (Physica B: Condensed Matter, vol. 541, pages 32-42, 2018) discloses a crystalline form of L-serine (hereinafter referred to as crystalline form A) having an X-ray diffraction pattern as shown in FIG. 15.

The present inventors have confirmed that there are problems in the process of preparing and formulating amorphous and crystalline forms of L-serine in that since L-serine is highly hygroscopic, care must be taken to avoid contact with moisture during handling processes such as storage and transportation, and when manufacturing finished pharmaceuticals and that it discolors into a yellow oxidized form when stored at a relatively low temperature of 40° C. for 5-7 days. Additionally, in the case of L-serine, it was confirmed that the increase in hygroscopicity not only has the disadvantage of hardening the surface of the powder in contact with moisture, which significantly reduces its dissolution rate in water, but also affect saturated solubility by the influence of excipients such as thickeners and sweeteners that are essentially used when preparing liquid formulations such as syrups, thereby causing technical difficulties in controlling pharmacokinetic properties.

Under the conditions, in order to solve the above-identified problems, the present inventors provide a novel crystalline form of L-serine with improved stability through improved hygroscopicity, thereby having improved properties of storage and handling, and improved dissolution rate, solubility, and pharmacokinetic characteristics, and a method of preparing the same.

DISCLOSURE OF INVENTION

Technical Problem

An object of the present invention is to provide a novel crystalline form of L-serine with improved stability through improved hygroscopicity, thereby having improved properties of storage and handling, and improved dissolution rate, solubility, and pharmacokinetic characteristics.

Another object of the present invention is to provide a method for preparing a novel crystalline form of L-serine.

Solution to Problem

[1] In one aspect of the present invention, the present invention relates to crystalline form L-serine represented by Formula 1 below, wherein the crystalline form has diffraction peaks at diffraction angles (2θ) of 19.06, 20.76, 22.86, 28.28, and 30.58 in X-ray powder diffraction analysis:

[Formula 1]

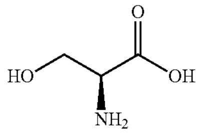

[2] In the [1] above, the crystalline form of L-serine may have an additional diffraction peak at one or more diffraction angles (2θ) selected from the group consisting of 18.49, 36.89, 42.13, 42.96, and 44.17.

[3] In the [1] above, the crystalline form of L-serine may show an endothermic point of 218.36° C. in differential scanning calorimetry analysis.

[4] In the [1] above, the crystalline form of L-serine may have absorption peaks of the infrared spectral spectrum at 3,457 $cm^{-1}$, 2,940 $cm^{-1}$, 1,572 $cm^{-1}$, 1,500 $cm^{-1}$, 1,466 $cm^{-1}$, 1,408 $cm^{-1}$, 1,123 $cm^{-1}$, 1,082 $cm^{-1}$, and 1,008 $cm^{-1}$.

[5] In one aspect of the present invention, the present invention relates to a method for preparing the crystalline form of L-serine according to the [1] above, which includes (a) mixing and stirring L-serine and a solvent; and (b) filtering the crystals produced after the stirring.

[6] In the [5] above, the solvent may be one or more selected from the group consisting of water, methanol, and ethanol.

[7] In the [5] above, when the solvent is a mixed solvent of water and methanol or a mixed solvent of water and ethanol, a mixing ratio may be 1:9 to 9:1.

[8] In the [5] above, a filtration temperature may be 10° C. or below.

[9] In the [5] above, (c) drying after the filtration may be further included.

[10] In the [9] above, a drying temperature may be 40-50° C.

[11] In the [9] above, a drying time may be 3-8 hours.

[12] In the [1] above, the crystalline form of L-serine may have the X-ray powder diffraction values shown in FIG. 3.

[13] In the [1] above, the crystalline form of L-serine may have the infrared spectral spectrum values shown in FIG. 6.

Advantageous Effects of Invention

The novel crystalline form (hereinafter referred to as type 1 crystalline form) of L-serine according to the present invention with improved stability through improved hygroscopicity, thereby having improved properties of storage and handling, and improved dissolution rate, solubility, and pharmacokinetic characteristics, and thus can be usefully used in the manufacture of pharmaceutical preparations.

In particular, the novel crystalline form of L-serine has little hardening phenomenon and thus can exhibit a fast dissolution rate in an aqueous solution, and it is less denatured by heat, and thus can inhibit the generation of related substances or discoloration in preparations containing the same.

BRIEF DESCRIPTION OF DRAWINGS

FIG. 1 is an X-ray powder diffractogram of amorphous form of L-serine.

FIG. 2 is an X-ray powder diffractogram of type A crystalline form of L-serine.

FIG. 3 is an X-ray powder diffractogram of type 1 crystalline form of L-serine.

FIG. 4 is an IR analysis diagram of amorphous form of L-serine.

FIG. 5 is an IR analysis diagram of type A crystalline form of L-serine.

FIG. 6 is an IR analysis diagram of type 1 crystalline form of L-serine.

FIG. 7 is a dynamic vapor adsorption/desorption curves as a result of dynamic vapor absorption (DVS) analysis of amorphous form of L-serine.

FIG. 8 is a dynamic vapor adsorption/desorption curve as a result of dynamic vapor absorption (DVS) analysis of type A crystalline form of L-serine.

FIG. 9 is a dynamic vapor adsorption/desorption curve as a result of dynamic vapor absorption (DVS) analysis of type 1 crystalline form of L-serine.

FIG. 10 is a differential scanning calorimetry analysis diagram of type 1 crystalline form of L-serine.

FIG. 11 is a differential scanning calorimetry analysis of amorphous form of L-serine.

FIG. 12 shows pharmacokinetic results of amorphous form of L-serine, type A crystalline form of L-serine, and type 1 crystalline form of L-serine in mice.

FIG. 13 shows the color change results of amorphous form of L-serine, type A crystalline form of L-serine, and type 1 crystalline form of L-serine after 8 weeks.

FIG. 14 shows the comparison results of type A crystalline form of L-serine and type 1 crystalline form of L-serine by overlapping their X-ray powder diffractograms.

FIG. 15 is an X-ray diffraction pattern of an existing crystalline form of L-serine (crystalline form A) disclosed in Document 2 (Physica B: Condensed Matter, vol. 541, pages 32-42, 2018).

DETAILED DESCRIPTION FOR CARRYING OUT THE INVENTION

Unless otherwise defined, all technical and scientific terms used in this specification have the same meaning as commonly understood by those skilled in the art to which the present invention pertains. In general, the nomenclature used herein is well known and commonly used in the art.

In one aspect, the present invention relates to a crystalline form of L-serine represented by Formula 1 below (type 1 crystalline form).

[Formula 1]

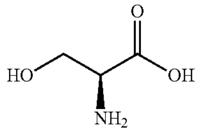

5

6

In the present invention, "L-serine", which is a type of amino acid constituting a protein, is a monoamide of glutamic acid, and is an L-amino acid having the structure of Formula 1 above.

In an embodiment of the present invention, the crystalline form of L-serine represented by Formula 1 has diffraction peaks at diffraction angles (2θ) of 19.06, 20.76, 22.86, 28.28, and 30.58 in X-ray powder diffraction analysis.

In another embodiment of the present invention, in X-ray powder diffraction analysis, the diffraction peaks with diffraction angles (2θ) where $I/I_0$ (I: intensity of the peak at each diffraction angle, $I_0$: intensity of the largest peak) is 10% or more may be at 19.06, 20.76, 22.86, 28.28, and 30.58.

In an embodiment of the present invention, the crystalline form of L-serine represented by Formula 1 may further have a diffraction peak at one or more diffraction angles (2θ) selected from the group consisting of 18.49, 36.89, 42.13, 42.96, and 44.17.

In one embodiment of the present invention, the crystalline form of L-serine represented by Formula 1 may have the X-ray powder diffraction analysis values as set forth in FIG. 3.

In another embodiment of the present invention, during X-ray powder diffraction analysis, the diffraction peaks with the diffraction angles (2θ) where $I/I_0$ is less than 10% may be at 18.49, 36.89, 42.13, 42.96, and 44.17.

In an embodiment of the present invention, the crystalline form of L-serine represented by Formula 1 may exhibit an endothermic point of about 218.36° C. in the analysis of differential scanning calorimetry. Therefore, the crystalline form of L-serine represented by Formula 1 has excellent thermal stability with a thermal decomposition temperature of about 218.36° C., and the active ingredient can remain stable without decomposition or discoloration even when it is stored for a long period of time.

In an embodiment of the present invention, the crystalline form of L-serine represented by Formula 1 may exhibit absorption peak values at 3,457 cm$^{-1}$, 2,940 cm$^{-1}$, 1,572 cm$^{-1}$, 1,500 cm$^{-1}$, 1,466 cm$^{-1}$, 1,408 cm$^{-1}$, 1,123 cm$^{-1}$, 1,082 cm$^{-1}$, and 1,008 cm$^{-1}$ in the infrared spectral spectrum (IR).

In one embodiment of the present invention, the crystalline form of L-serine represented by Formula 1 may have the infrared spectral spectrum values as set forth in FIG. 6.

In another aspect, the present invention relates to a method for preparing a crystalline form of L-serine represented by Formula 1, which includes (a) mixing and stirring L-serine and a solvent; and (b) filtering the crystals produced after the stirring.

In an embodiment of the present invention, "L-serine" used in the step (a) is a compound represented by Formula 1, and may be L-serine prepared by a known method. Conventionally, L-serine was mostly prepared by fermentation or by preparing a DL-serine mixture using mercury, and the like and then obtaining pure L-serine through optical resolution. Representatively, as a method for preparing serine in a literature (*Advances in Biochemical Engineering/Biotechnology* 79 (2003) 1), there is disclosed a method for preparing 45 g/L of L-serine along with 88 g/L methanol from 100 g/L of glycine using *Hyphomicrobium* sp. NCIB10099 over 3 days. In another literature (U.S. Pat. No. 5,382,517), there is disclosed a preparation method for obtaining a yield of 89% by fermenting an aqueous solution of glycine and formaldehyde (485 g/L) using *Escherichia coli* MT-10350 at 50° C. for 35 hours. As another preparation method, a literature [*Org. Synth.* 1940, 20, 81] discloses a preparation method using acrylate as a starting material.

In an embodiment of the present invention, the form of L-serine used in the step (a) is not limited, and for example, the L-serine may be oil-like L-serine obtained by concentrating the solvent after preparing L-serine, or amorphous or type A crystalline form of L-serine.

In the step (a), the "solvent" may be a polar solvent, and specifically, may be one or more selected from the group consisting of water, methanol, and ethanol.

In an embodiment of the present invention, when the solvent is a mixed solvent of water and methanol or a mixed solvent of water and ethanol, a mixing ratio may be 1:9 to 9:1.

In addition, the amount of the solvent may be about 3-20 times the amount of L-serine used in production, preferably about 4-15 times, and most preferably about 5-10 times, considering the economic efficiency of the process.

In an embodiment of the present invention, in the step (a) above, L-serine is dissolved when L-serine and the solvent are mixed; when dissolving, the temperature does not need to be raised from room temperature, but the temperature may be raised when necessary; and considering the economic efficiency of the process and prevention of discoloration, it is most desirable that the dissolving is proceeded at about 50° C. or below.

In an embodiment of the present invention, after stirring in the step (a) above, concentrating and removing the solvent and gradually lowering the temperature for crystallization may be further included. When too little solvent is removed in the process of concentrating and removing the solvent, the process yield will decrease, whereas when too much of the solvent is removed, it will not only increase the preparation time thereby making it less economical, but also entails a risk of bumping during the process of concentrating the solvent under reduced pressure. Therefore, it is most desirable to concentrate the solvent when about ⅖-½ of the total solvent is left.

Meanwhile, the cooling temperature in the crystallization is preferably about –5-30° C., more preferably about 0-20° C., and most preferably about 5-15° C.

In an embodiment of the present invention, in the step (b), any tool capable of performing a filtration function may be used. For example, on a relatively small scale, a Buchner funnel may be used, and in industrial terms, production efficiency may be increased by performing the process under reduced pressure using a Nutsche filter, but the process is not limited to thereto. Additionally, the temperature for filtration may be about 10° C. or below.

In an embodiment of the present invention, (c) drying after the filtration may be further included, and the drying temperature may be about 40-50° C., but the drying temperature is not limited thereto, and drying time may appropriately be set considering economic efficiency, preferably about 12 hours or less, and most preferably about 3-8 hours.

The novel type 1 crystalline form of L-serine according to the present invention, due to relatively lower hygroscopicity and reduced hardening compared to amorphous form of L-serine or type A crystalline form of L-serine, shows a fast dissolution rate in an aqueous solution, and exhibits higher solubility in a syrup solution; therefore, it can be usefully used in the manufacture of a pharmaceutical preparation. In particular, the type 1 crystalline form of L-serine, due to its low susceptibility to heat denaturation, not only can inhibit the generation of related substances or discoloration in preparations containing the same, but also, due to its low hygroscopicity thereof, can allow raw material storage and manufacturing processes to be performed at room temperature with a relative humidity of 60%, thus being convenient. Additionally, the type 1 crystalline form of L-serine exhibits excellent pharmacokinetic properties than amorphous form of L-serine or type A crystalline form of L-serine; therefore, a therapeutic effect can be expected with a smaller amount of L-serine.

Hereinafter, in order to help understanding of the present invention, it will be described in detail using Examples. However, Examples according to the present invention may be modified into various other forms, and the scope of the present invention should not be construed as being limited to the following Examples. Examples of the present invention are provided to more completely explain the present invention to those with average knowledge in the field to which the present invention pertains.

EXAMPLES

Comparative Example 1: Preparation of Amorphous Form of L-Serine

The L-serine, which was obtained by dissolving 100 g of O-acetyl-L-serine (Aldrich, 99% purity) in 500 mL of water, adding 3 mL of acetic acid, followed by stirring at 70° C. for 6-8 hours, concentrating the solvent under reduced pressure, and freeze-drying, was subjected to X-ray powder diffraction analysis and the results are shown in FIG. 1, and the infrared spectral (IR) data are shown in FIG. 4, and differential scanning calorimetry data is shown in FIG. 11, from which it was confirmed that the L-serine was amorphous.

Comparative Example 2: Preparation of Type a Crystalline Form of L-Serine

Crystalline form A of L-serine was prepared with a yield of 70% according to the preparation method in Non-Patent Document 2.

250 g of L-serine (purchased from Aldrich) was added and dissolved in 100 mL of water. The resultant was heated to 60-70° C. and stirred for 6 hours. After complete dissolution, the resultant was cooled to 5-10° C., stirred for 1 hour, and then filtered to obtain pure L-serine as a white solid.

The obtained L-serine was subjected to X-ray powder diffraction analysis, and the results are shown in FIG. 2, infrared spectral (IR) data in FIG. 5, and differential scanning calorimetry data in FIG. 10.

Example 1: Preparation of Crude L-Serine 355 g of DL-serine (purchased from Aldrich) and 232 g of L-(−)camphorsulfonic acid (purchased from EOS, China) were added and dissolved in 2,200 mL of ethyl acetate (purchased from Samchun Chemicals). The resultant was heated to 80-90° C. and stirred for 3 hours. After completion of the reaction, the mixture was cooled to 5-10° C., stirred for 1 hour, and then filtered to obtain pure L-serine-camphorsulfonic acid as a white solid. The obtained solid was dissolved in 120 L of anhydrous ethanol and aqueous ammonia was added thereto to adjust the pH to between 6.0 and 7.0. The reactants were stirred at room temperature for 1.5 hours, cooled to 5-10° C., stirred for additional 3 hours, and then filtered to obtain 150 g of crude L-serine as an off-white solid.

Example 2: Preparation of Novel Crystalline Form of L-Serine (1)

After dissolving 50 g of the amorphous form of L-serine prepared in Comparative Example 1 above in 0.40 L of water followed by stirring, about ½ of the solvent was removed by concentration, and the resultant was cooled to a temperature of 10° C. or below, and the resulting solid was filtered, and dried under vacuum at 40° C. for 6 hours to obtain type 1 crystalline form of L-serine with a yield of 74%.

The obtained crystalline form of L-serine was subjected to X-ray powder diffraction analysis, IR analysis, differential scanning calorimetry, and DVS analysis, and the results are shown in FIGS. 3, 6, 10, and 9, respectively. FIG. 14 shows the result of overlapping the X-ray powder diffraction patterns of type A crystalline form of L-serine obtained in Comparative Example 2 and type 1 crystalline form of L-serine obtained in Example 2. From FIG. 14, it can be seen that type A crystalline and type 1 crystalline are mutually-different crystalline types.

Example 3: Preparation of Novel Crystalline Form of L-Serine (2)

After dissolving 50 g of crude L-serine from Example 1 in 0.40 L of water followed by stirring, about ½ of the solvent was removed by concentration, and the resultant was cooled to a temperature of 10° C. or below, and the resulting solid was filtered, and dried under vacuum at 40° C. for 6 hours to obtain type 1 crystalline form of L-serine with a yield of 85%.

As a result of performing X-ray powder diffraction analysis and differential scanning calorimetry analysis of the obtained crystalline form, it was confirmed that the L-serine was in the same form of crystals as in Example 2.

Example 4: Preparation of Novel Crystalline Form of L-Serine (3)

After dissolving 30 g of type A crystalline form of L-serine prepared in Comparative Example 2 in 0.50 L of water followed by stirring, about ½ of the solvent was removed by concentration, and the resultant was cooled to a temperature of 10° C. or below, and the resulting solid was filtered, and dried under vacuum at 40° C. for 7 hours to obtain type 1 crystalline form of L-serine with a yield of 60%.

As a result of performing X-ray powder diffraction analysis and differential scanning calorimetry analysis of the obtained crystalline form, it was confirmed that the L-serine was in the same form of crystals as in Example 2.

Example 5: Preparation of Novel Crystalline Form of L-Serine (4)

After dissolving 50 g of crude L-serine from Example 1 in 0.40 L of water/methanol (9/1) followed by stirring, about ½ of the solvent was removed by concentration, and the resultant was cooled to a temperature of 10° C. or below, and the resulting solid was filtered, and dried under vacuum at 40° C. for 6 hours to obtain type 1 crystalline form of L-serine with a yield of 77%.

As a result of performing X-ray powder diffraction analysis and differential scanning calorimetry analysis of the

9 obtained crystalline form, it was confirmed that the L-serine was in the same form of crystals as in Example 2.

Example 6: Preparation of Novel Crystalline Form of L-Serine (5)

After dissolving 50 g of crude L-serine from Example 1 in 0.40 L of water/methanol (9/1) followed by stirring, about ½ of the solvent was removed by concentration, and the resultant was cooled to a temperature of 10° C. or below, and the resulting solid was filtered, and dried under vacuum at 40° C. for 6 hours to obtain type 1 crystalline form of L-serine with a yield of 79%.

As a result of performing X-ray powder diffraction analysis and differential scanning calorimetry analysis of the obtained crystalline form, it was confirmed that the L-serine was in the same form of crystals as in Example 2.

Example 7: Preparation of Novel Crystalline Form of L-Serine (6)

After dissolving 200 g of O-acetyl-L-serine (Aldrich, 99% of purity) in 100 mL of water, one drop of acetic acid was added thereto, and the mixture was stirred at 70° C. for 6 hours, and about ½ of the solvent was removed by concentration, and the resultant was cooled to a temperature of 10° C. or below, and the resulting solid was filtered, and dried under vacuum at 40° C. for 8 hours to obtain type 1 crystalline form of L-serine with a yield of 77%.

As a result of performing X-ray powder diffraction analysis and differential scanning calorimetry analysis of the obtained crystalline form, it was confirmed that the L-serine was in the same form of crystals as in Example 2.

X-Ray Powder Diffraction Analysis

The X-ray powder diffraction analysis (XRD) was performed using a powder X-ray diffraction detector to obtain a diffraction pattern in the range of 5-80° 2θ. The powder X-ray diffraction analysis conditions are as follows.

Equipment: EMPYREAN Panalytical
Time per step: 0.5 s
Scanning method: Continuous PSD fast
X-ray tube; Cu 1.8 KW
Detector: PIXcel3D (1D mode)

Differential Scanning Calorimetry Analysis

Differential scanning calorimetry (DSC) was performed using a SCINCO DSC N-650 model. About 2-3 mg of a sample was placed in an aluminum pan and covered with a perforated lid to prepare a sample required for the DSC experiment. After recording the exact weight of the sample, it was heated to 30-350° C. at a rate of 10° C./min under nitrogen.

Saturation Solubility Test Based on Raw Material

Each raw material was prepared and tested as a 2,000 mg/mL solution of L-serine (MW=105.09) according to the following test method, and the amount was measured three times using the following method.

a. 10.0 g of each raw material as L-serine is added into a 50 mL conical tube, and then about 5 mL of purified water (or a syrup composition) is added thereto, and the mixture is vigorously mixed using a vortexer for 30 seconds.

b. The resulting solution is left at room temperature for 5 minutes and then is mixed vigorously using a vortexer for 30 seconds.

c. The process b is repeated 6 times (about 30 minutes) and then the resultant is left at room temperature until the floating materials are settled.

10 d. The supernatant of the solution is placed into a 2.0 mL EP tube and is subject to perform centrifugation using a centrifuge at 23° C. and 4,000 rpm for 20 minutes.

e. 1 mL of the supernatant of the solution is taken and placed into a 100 mL volumetric flask, and purified water is filled to the mark. Then, 5 mL (or 10 mL) of this solution is taken, and placed into a 50 mL volumetric flask, purified water is filled to the mark and used as a test solution.

f. The test solution is analyzed according to HPLC operating conditions for the test of L-serine content.

Experimental Example 1: Thermal Stability Test 8 mg of each L-serine obtained in Comparative Examples 1, 2, and Example 3 was placed into an opaque glass vial and stored at 40±2° C., 75±5% RH. After 8 weeks, each sample was taken out and the content was analyzed using high-performance liquid chromatography (HPLC), and the presence of discoloration was visually confirmed as shown in FIG. 13.

High-Performance Liquid Chromatography Conditions

Equipment: Waters Alliance e2695
Column: SIELC Primsep 100, 150 mm×4.6 mm×5 µm
Column temperature: 30° C.
Flow rate: 1.0 mL/min
Detection: 210 nm, UV
Injection volume: 10 µL
Total analysis time: 40 mins
Mobile phase: Adjust the pH to 2.2±0.05 using phosphoric acid in 1,000 mL of water.

As a result of the 8-week analysis, it was confirmed that the crude L-serine obtained in Comparative Examples 1 and 2 showed a decrease in L-serine content or discoloration compared to the standard product, and the type 1 crystalline form of L-serine obtained in Example 3 was confirmed to exhibit excellent stability for up to 8 weeks without any change in content value or color of powder. When the change in crystal form of L-serine was confirmed through XRD after 8 weeks, some of the amorphous cases changed into crystalline forms, and the type A crystalline form of L-serine obtained in Comparative Example 2 and the type 1 crystalline form of L-serine obtained in Example 3 showed no change in crystal form. These results are shown in Table 1 below.

TABLE 1

| | Storage conditions 40° C./75% RH | | |
| --- | --- | --- | --- |
| | Comparative Example 1 (amorphous) | Comparative Example 2 (type A crystalline) | Example 3 (type 1 crystalline) |
| L-serine content from 0 week → after 8 weeks | 99.0% → 90.4% | 99.1% → 93.7% | 99.3% → 99.2% |
| Discoloration/ Change in Crystal | change to off-white color change in part to crystal form | change to off-white color crystal form retained | no change in color crystal form retained |

As shown in Table 1 above, type 1 crystalline according to Example 3 was confirmed to be stable without any decrease in content due to hygroscopicity or discoloration due to oxidation.

Experimental Example 2: Hygroscopicity Test

The amorphous and the type A crystalline forms of L-serine obtained in Comparative Examples 1 and 2, respectively, and the type 1 crystalline form of L-serine obtained in Example 3 were each tested by repeating absorption and dehumidification once at 5% RH intervals in the range of 2-98% relative humidity under an isothermal condition of 25° C. using a dynamic vapor absorption (DVS) device (VTI SGA-100, TA Instruments), which is a dynamic vapor adsorption and desorption device. The adsorption and desorption behavior of moisture according to relative humidity are shown in FIGS. 7 to 9, respectively.

As a result of DVS analysis, the amorphous form of L-serine obtained in Comparative Example 1 started to absorb moisture already at a relative humidity of 40%, as shown in FIG. 7, and the type A crystalline form of L-serine obtained in Comparative Example 2 started to absorb moisture at a relative humidity of around 70% as shown in FIG. 8, whereas type 1 crystalline form of L-serine obtained in Example 3 started to absorb moisture at a relative humidity of around 80% as shown in FIG. 9; therefore, it was confirmed that type 1 crystalline form of L-serine exhibits relatively low hygroscopicity.

Experimental Example 3: Pharmacokinetic Comparison

After fasting for 12 hours, blood samples were collected at 6, 4, 2, and 0 hours before drug administration, each crystalline form of L-serine was administered once (400 mg/kg, n=5) using a sonde for oral administration, and about 40-50 μL of blood was collected and measured at 0.25, 0.5, 1, 3, 6, 9, and 12 hours after drug administration. The measurement results are shown in FIG. 12, and the results after baseline correction of L-serine are shown in Table 2.

As a result, as shown in Table 2 and FIG. 12, it was confirmed that the type 1 crystalline form of L-serine prepared in Example 3 showed no significant difference in the maximum blood concentration ($C_{max}$) between drugs after drug administration compared to amorphous form and type A crystalline form of L-serine prepared in Comparative Example 1 and 2, respectively; however, the half-life ($T_{1/2}$) of the drug was significantly different depending on the crystal form, and in the case of type 1 crystalline form of L-serine, the drug concentration in the 0-12 hour concentration-time curve ($AUC_{0-12}$) was increased by about 2 times or more compared to amorphous form and type A crystalline form of L-serine.

TABLE 2

Comparison table of pharmacokinetics after baseline correction

| Parameter | Unit | Comparative Example 1 | Comparative Example 2 | Example 3 |
|---|---|---|---|---|
| $t_{1/2}$ | h | 4.15 ± 0.99 | 2.56 ± 0.76 | 3.56 ± 1.36 |
| $T_{max}$ | h | 0.25 | 0.50 | 0.50 |
| $C_{max}$ | μg/mL | 67.5 ± 25.92 | 77.69 ± 8.49 | 75.48 ± 10.70 |
| $AUC_{0-12}$ | μg/mL*h | 100.53 ± 20.15 | 165.81 ± 40.99 | 248.89 ± 37.34 |
| $AUC_{0-inf}$ | μg/mL*h | 121.45 ± 17.20 | 177.36 ± 39.9 | 296.22 ± 69.63 |
| $MRT_{0-inf}$ | h | 5.11 ± 0.8 | 3.44 ± 1.49 | 5.29 ± 2.10 |
| Vz/F | (mg/kg)/(μg/mL) | 19.87 ± 4.89 | 11.69 ± 4.25 | 9.91 ± 1.97 |
| CI/F | (mg/kg)/(μg/mL)/h | 3.35 ± 0.43 | 3.19 ± 0.67 | 2.11 ± 0.49 |

Experimental Example 4. Measurement of Saturated Solubility of Each Crystalline Form of L-Serine in Purified Water For each crystalline form of L-serine, the saturated solubility was measured while observing the dissolution rate using purified water as a solvent, and the results are shown in Table 4.

a. 10.0 g of each L-serine obtained in Comparative Example 1, Comparative Example 2, and Example 3 are added into a 50 mL conical tube, and then about 5 mL of purified water is added thereto, and the mixture is vigorously mixed using a vortexer for 30 seconds.

b. The resulting solution is left at room temperature for 5 minutes and then vigorously mixed using a vortexer for 30 seconds.

c. The process b is repeated 6 times (about 30 minutes) and then the resultant is left at room temperature until the floating materials are settled.

d. The supernatant of the solution is placed into a 2.0 mL eppendorf tube and is subject to perform centrifugation using a centrifuge at 23° C. and 4,000 rpm for 20 minutes.

e. 1 mL of the supernatant of the solution is taken and placed into a 100 mL volumetric flask, and purified water is filled to the mark. Then, 5 mL (or 10 mL) of this solution is taken and placed into a 50 mL volumetric flask, purified water is filled to the mark, and used as a test solution.

f. The test solution is analyzed according to HPLC operating conditions for the test of L-serine content.

Experimental Example 5. Measurement of Saturated Solubility of Each Crystalline Form of L-Serine in Syrup Solution For each crystalline form of L-serine, the saturated solubility was measured while observing the dissolution rate using a solution in a syrup formulation as a solvent, and the results are shown in Table 4.

The composition of the syrup agent was prepared using the method specified in Korean Patent Application No. 10-2022-0033655, as shown in Table 3 below, and the experiment method for saturation solubility was performed in the same manner as in Experimental Example 4, but the solution of a syrup agent composition in Table 3 was used instead of the purified water in Experimental Example 4.

TABLE 3

| Content (amount (mg) in 1 mL) | | |
|---|---|---|
| Diluent | D-Sorbitol solution | 30.0 |
| Thickener | Carbomer 971P | 4.0 |

TABLE 3-continued

| Content (amount (mg) in 1 mL) | | |
|---|---|---|
| Flavoring agent | Apple mint scent SJ-G (22005221) | 2.0 |
| Preservative | Methyl paraoxybenzoate | 0.05 |
| | Paraoxybenzoic acid propyl | 0.05 |
| Sweetener | Refined white sugar | 80.0 |
| Acidifying agent | Citric acid hydrate | 0.3 |
| Buffer | Potassium citrate hydrate | 1.5 |
| Solvent | Purified water | q.s. |
| | Final pH | 5.4 |

As shown in Table 4 below, it was confirmed that the average solubility of the novel type 1 crystalline form of L-serine in water was almost the same as that of the amorphous form and the type A crystalline form of L-serine, but the average solubility in the syrup composition was 5-10% higher than those of amorphous form and the type A crystalline form of L-serine, and that the dissolution speed was fast in the dissolution rate and the dissolution process went smoothly because there was no hardening phenomenon compared to the amorphous form and crystalline form of L-serine.

TABLE 4

| | Sample name | Average solubility in aqueous solution (mg/mL) | Average solubility in syrup composition (mg/mL) | Remark |
|---|---|---|---|---|
| 1 | Comparative Example 1 | 300.4 | 207.7 | The first addition of purified water resulted in hardening of the crystals; therefore, the vortexing time was increased to 2 minutes and the standing time was increased to 8 minutes. |
| 2 | Comparative Example 2 | 299.0 | 195.9 | The first addition of purified water resulted in hardening of the crystals; therefore, the vortexing time was increased to 3 minutes and the standing time was increased to 10 minutes. |
| 3 | Example 3 | 300.6 | 220.1 | The procedure went smoothly smoothly within a predetermined time without occurrence of a hardening phenomenon. |

Accordingly, the novel type 1 crystalline form of L-serine, which has relatively lower hygroscopicity and reduced hardening compared to amorphous form or type A crystalline form of L-serine, exhibits a faster dissolution rate than in an aqueous solution, and thus can be usefully used in the manufacture of pharmaceutical preparations. In particular, since the type 1 crystalline form of L-serine is less susceptible to heat denaturation, not only it can inhibit the generation of flexible substances or discoloration in preparations containing the same, but also, due to low hygroscopicity, can allow the storage of raw materials and the performance of a manufacturing process at room temperature with a relative humidity of 60%, thus being convenient. In addition, the novel type 1 crystalline form of L-serine exhibits improved pharmacodynamic characteristics compared to amorphous form or type A crystalline form of L-serine; therefore, a therapeutic effect can be expected with a smaller amount of L-serine.

The invention claimed is:

1. A crystalline form of L-serine represented by Formula 1 below:

[Formula 1]

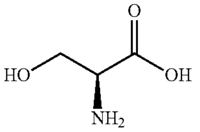

wherein the crystalline form has diffraction peaks at diffraction angles (2θ) of 19.06, 20.76, 22.86, 28.28, and 30.58 as determined by X-ray powder diffraction, and wherein the crystalline form has an additional diffraction peak at one or more diffraction angles (2θ) selected from the group consisting of 18.49, 36.89, 42.13, 42.96, and 44.17.

2. The crystalline form of L-serine of claim 1, which shows an endothermic point of 218.36° C. as determined by differential scanning calorimetry.

3. The crystalline form of L-serine of claim 1, which has absorption peaks of an infrared spectral spectrum at 3,457 $cm^{-1}$, 2,940 $cm^{-1}$, 1,572 $cm^{-1}$, 1,500 $cm^{-1}$, 1,466 $cm^{-1}$, 1,408 $cm^{-1}$, 1,123 $cm^{-1}$, 1,082 $cm^{-1}$, and 1,008 $cm^{-1}$.

4. A method for preparing the crystalline form L-serine according to claim 1, comprising:

(a) mixing and stirring L-serine and a solvent to form crystals; and (b) isolating, by filtration, the crystals produced after the stirring.

5. The method of claim 4, wherein the solvent is one or more selected from the group consisting of water, methanol, and ethanol.

6. The method of claim 4, wherein the solvent is a mixed solvent of water and methanol or a mixed solvent of water and ethanol, and wherein a mixing ratio of water and methanol or ethanol is 1:9 to 9:1.

7. The method of claim 4, wherein a filtration temperature is 10° C. or below.

8. The method of claim 4, further comprising (c) drying after the filtration.

9. The method of claim 8, wherein a drying temperature is 40-50° C.

10. The method of claim 8, wherein a drying time is 2-7 hours.

11. The crystalline form of L-serine of claim 1, having the X-ray powder diffraction values of FIG. 3.

12. The crystalline form of L-serine of claim 1, having the infrared spectral spectrum values of FIG. 6.

* * * * *